United States Patent [19]  [11] 4,268,494
Reese  [45] * May 19, 1981

[54] AUTOMATED DIRECT SERUM RADIOASSAY

[75] Inventor: Max Reese, Salt Lake City, Utah

[73] Assignee: Becton Dickinson & Company, Paramus, N.J.

[*] Notice: The portion of the term of this patent subsequent to Aug. 22, 1995, has been disclaimed.

[21] Appl. No.: 920,801

[22] Filed: Jun. 30, 1978

Related U.S. Application Data

[63] Continuation-in-part of Ser. No. 774,390, Mar. 4, 1977, Pat. No. 4,108,976.

[51] Int. Cl.$^2$ .................... G01N 33/16; A61K 43/00
[52] U.S. Cl. .................... 424/1; 23/230 B; 422/71; 424/12
[58] Field of Search .................... 424/1, 12; 23/230 B; 422/50, 71, 101

[56] References Cited

U.S. PATENT DOCUMENTS

| | | | |
|---|---|---|---|
| 3,896,217 | 7/1975 | Johnson | 424/1 |
| 3,940,475 | 2/1976 | Gross | 424/1 |
| 3,950,134 | 4/1976 | Miles | 23/230 B |
| 3,950,643 | 4/1976 | Charlton | 424/1 X |
| 3,989,383 | 11/1976 | Paulson | 23/230 B X |
| 4,009,005 | 2/1977 | Johnson | 23/253 R |
| 4,022,577 | 5/1977 | Brooker | 23/230 B |
| 4,108,976 | 8/1978 | Reese | 424/1 |

*Primary Examiner*—Richard E. Schafer
*Assistant Examiner*—Christine M. Nucker
*Attorney, Agent, or Firm*—Louis E. Marn; Elliot M. Olstein

[57] ABSTRACT

Automated radioassay in which a serum is diluted and pre-incubated in the presence of a radioactive labeled ligand, such as an antigen, and a binder, such as an antibody, specific to the ligand. The pre-incubated mixture is flowed through a chamber containing binder specific to the ligand supported on a solid support, and the labeled and unlabeled ligand not bound to the binder in pre-incubation are bound to the receptor on flow through the chamber. An eluting solution is flowed through the chamber to release the ligand bound to the binder in the chamber for reuse thereof. By counting the radioactivity of one or both of the fraction which flows through the chamber or which is subsequently released therefrom the quantity of a specific ligand in the serum may be assayed.

7 Claims, No Drawings

AUTOMATED DIRECT SERUM RADIOASSAY

This application is a continuation-in-part of U.S. Application Ser. No. 774,390, filed Mar. 4, 1977, now U.S. Pat. No. 4,108,976.

This invention relates to a radioassay, and more particularly to an improved method for the direct assay of a ligand in a serum by an automated procedure.

U.S. Pat. No. 3,896,217 of July 22, 1975, disclosed an assay in which antibodies covalently bound to a substrate are used to bind antigen, followed by release of antigen by flowing an eluting solution through the antibodies. By this system, the antibodies may be reused repeatedly.

An automated apparatus is described in U.S. Pat. No. 4,009,005 as a continuation-in-part of U.S. Pat. No. 3,896,217 setting forth in more detail the various aspects of the equipment for the automated radioassay by use of a reusable immobilized immunoadsorbent.

U.S. Pat. No. 4,059,685 describes an improved immunoadsorbent and methods of making and using the same. As there described, the immunoadsorbent includes a particulate substrate having bonded thereto by covalent bonds the antibody specific to the antigen.

Since the systems of the above patents and applications relate principally to a flow-through type of system, one of the practical aspects of the technology is the flow-through character of the various mixtures which pass into and through the immobilized immunoadsorbent. More particularly, if the materials flowing through the immobilized immunoadsorbent, usually placed in a chamber, tend to plug up the flow passages, the use and reuse of the chamber is adversely affected. Such adverse effects are manifest in several different ways including physically plugging to prevent flow, or by slowing the flow through the chamber sufficiently to extend unreasonably the time for what should be a relatively rapid automative assay, or both.

As will be appreciated, plugging is a characteristic only of those immunoadsorbents which are reusable. With single use immunoadsorbents, to be described, the flow through and repeated flow through of material is not of major consequence.

One source of plugging are the proteins, other than the antigen, which may be present in a sample. While the chamber includes a screen to filter out large components, the proteins may pass through the screen and accumulated in the intenstices of the particulate substrate especially if that substrate is of the type described in U.S. Pat. No. 3,505,785 of Apr. 14, 1970, a substrate which is desirable because each particle is a macroparticle with an impervious core having a coating of monolayers of colloidal microparticles thereby providing a substantial surface area.

A typical source of plugging proteins is serum, i.e., blood from which suspended cellular elements have been removed usually by centrifugation. Thus, if undiluted serum is assayed using an immunoadsorbent of the type described in the above referenced patent and patent applications, the relatively large proteins pass through the filter and tend to plug up the immunoadsorbent. The serum may be diluted to reduce the concentration of proteins for better flow through the immunoadsorbent. Dilution, however, also reduces the concentration of the antigens in the serum. Where the concentration of free antigen in serum is relatively low, e.g., digoxin and $T_3$, diluting the serum reduces the concentration even more and presents problems in accurately and reliably assaying for the relatively small amounts of antigen present in the diluted serum. Thus, dilution to avoid a plugging problem leads to problems of accurate assays, i.e., the sensitivity of the assay is less than desired.

In accordance with the present invention, there is provided an automatic radioassay for a ligand in a serum, at room temperature, while assuring proper flow through an immobilized specific binder. This is achieved while maintaining assay sensitivity; i.e., accuracy of assay at low levels of ligand.

Thus, radioactive labeled ligand and unlabeled diluted serum sample (or standard) ligand is pre-incubated with specific binder in a sample cup for a period of 30 minutes to 3 hours or more. Separation of free and bound ligand is accomplished on the equipment described in U.S. Pat. No. 4,009,005 previously identified. The antibody chamber includes an immobilized binder of a binder specific for the ligand supported on a solid support. The sample containing free ligand and ligand bound to the binder, as a result of the pre-incubation step, is passed through the chamber. Since the serum sample has been diluted, the concentration of proteins tending to plug the chamber is reduced and there is satisfactory free flow of the sample through the chamber.

During flow through the immobilized binder, the free ligand (labeled and unlabeled) binds to the binder bound to the support while the bound ligand; i.e., the labeled and unlabeled ligand bound to the binder in the pre-incubation step, passes through the chamber to a radioactive detector where it is counted. Subsequently, an eluting solution is flowed through the chamber to free the ligand bound to the immobilized binder. The ligand (labeled and unlabeled) freed from the immobilized binder by the eluting solution flows to a radioactive detector where it is counted. Following elution to free the ligand, the immobilized binder is rinsed and ready for reuse in the next and subsequent cycles.

By diluting the serum the problems of flow are substantially reduced in the sense that the material flowing through the chamber does not plug the chamber or the immobilized binder. Dilution, however, reduces the concentration of the ligand and thus creates sensitivity problems especially at the low concentration range of those ligands which are present in serum at low concentrations to begin with. By this invention, it has been discovered that sensitivity can be increased by the pre-incubation step with free binder and subsequent separation by a binder on a solid support. Thus, the immobilized binder includes adequate specific binder to assure that the free ligand is "captured".

The present invention is applicable to any one of a wide variety of assays for a wide variety of ligands for which an appropriate binder can be found, such as (1) antigens, which when introduced into the blood stream of a vertebrate, result in the formation of antibodies; (2) haptens, which when bound to an antigenic carrier and introduced into the blood stream of a vertebrate produce antibodies specific for the hapten (haptens are sometimes interchangeably referred to as antigens); or (3) substances which have naturally occurring binders; e.g., thyroxine binding globulin which is a binder for thyroxine, and triiodothyronine and other binders extracted from various animal organs, serums, milk binders and the like. It is also to be understood that in some cases, the ligand to be assayed is an antibody, in which case the binder would be an antigen.

As representative examples of ligands which can be assayed in accordance with the present invention, there may be mentioned: polypeptides, nucleotides, nucleosides and proteins, such as ACTH, oxytocin, lutenizing hormone, insulin, proinsuln, Bence-Jones protein, chorionic gonadotropin, pituitary gonadotropin, growth hormone, renin, thyroxine binding globulin, bradykinin, angiostensin, follicle stimulating hormone; cyclic AMP; cholylglycine, cyclic GMP, etc; steroids, including: estrogens, gestrogens, androgens, andrenocortical hormones, bile acids, cardiotonic glycosides, aglycones as well as saponins. As specific examples there may be mentioned: thyroxine, triiodothyronine, testosterone, androsterone, equilenin, estrone, estriol, progesterone, pregnenolone, 17-hydroxydioxycorticosterone (compound S), deoxycorticoserone, cortisone, corticosterone, cortisol, aldosterone, digoxin, digitoxin, etc.; vitamins, such as folic acid, the B vitamin group, the D vitamins, and miscellaneous ligands, such as antigens for Viral Hepatitis A and B, Rubella, Herpes Simplex, α-fetoprotein, etc.

The labeled ligand employed in the assay can be the ligand or an appropriate analog thereof, provided that the ligand to be assayed and labeled ligand are both specifically bound by the binder employed in the assay. The radioactive "label" or "tag" is a suitable radioisotope, such as a radioisotope of iodine, tritium, cobalt and the like.

Thus, in accordance with the present invention, the general sequence includes a pre-incubation step employing a binder specific for the ligand to be assayed, followed by a separation step employing an immobilized binder for the ligand to be assayed and a counting operation to determine the quantity of ligand to be assayed present in the serum. The invention will be further described with respect to an assay for an antigen, employing an antibody as the binder; however, such disclosure is equally applicable to the use of binders other than antibodies, as hereinabove described.

As will be appreciated, the quantity of antigen in a sample is related to standards of known concentration which are assayed to develop standard curves against which unknowns are compared. This may be done by computer as explained in U.S. Pat. No. 4,009,005 to which reference has been made. The generation of data from standards is accomplished by the same basic sequence used with unknowns. Accordingly, in the following discussion reference will be made to "sample" i.e., the antigen sample of unknown concentration, and to "standard" the sample of antigen of known concentration.

A known amount of radioactive labeled tracer antigen is admixed with a sample or standard and pre-incubated in the presence of an antibody specific to that antigen. This may be carried out in a polystyrene sample cup of about 2 ml total volume.

The pre-incubation time may vary but is normally in the range of 10 minutes to 3 hours or more, at a suitable temperature. During the pre-incubation, a portion of each of the labeled and unlabeled antigen sample or standard is bound to the antibody while the remainder of the labeled and unlabeled antigen is free. This mixture is then flowed through an immobilized immunoadsorbent, to be described, to effect separation of the labeled and unlabeled antigen bound to the antibody in the pre-incubation step and the labeled and unlabeled antigen which is free.

During flow through of the immunoadsorbent, the free fraction binds to the antibody which is immobilized on the substrate and the bound fraction (labeled and unlabeled antigen bound to antibody during pre-incubation) flows through the immunoadsorbent which may then be counted for radioactivity. Thereafter, the free fraction bound to the immobilized immunoadsorbent is freed by flowing an eluting solution through the immunoadsorbent to effect stoichiometric release of the fraction bound to the immobilized immunoadsorbent. The free fraction may then be counted for radioactivity. Standard data, in the case of standards, or determination of the amount of the sample by comparison with standard data may be generated from the counts, as is well known in the art.

Following elution, the immunoadsorbent is rinsed and is reused for further assays of the same antigen.

The immunoadsorbent may be placed in a chamber and may be of the type described in U.S. Pat. No. 4,059,685 to which reference has been made. Alternatively, the immobilized immunoadsorbent may be of the type set forth in U.S. Application Ser. No. 774,277 filed Mar. 4, 1977. Regardless of the specific form of the immobilized immunoadsorbent, it preferably includes a solid substrate, stable against hydration, and having binder supported thereon. Various techniques have been described in the pending application herein referred to by which antibodies may be covalently bound to a solid particulate support. With these types of immobilized immunoadsorbents, the bond between the antigen and the antibody bound to the support is broken by the eluting solution which does not adversely affect the covalent bond by which the antibody is bound to the support. Accordingly, the free antigen is stoichiometrically released and the immunoadsorbent may be reused repeatedly.

The repeated reuse of the immunoadsorbent and the particulate nature of the substrate creates problems of flow through if there are materials in the mixture which can plug up the immunoadsorbent. One source of plugging components is the proteins present in serum. While proteins may not present problems in a single use of an immunoadsorbent, where the immunoadsorbent is to be repeatedly reused, as is the case in an automated radioimmunoassay system contemplated by this invention, these proteins may create problems.

Thus in accordance with this invention, the serum sample is diluted, but in doing so there may be dilution of some of the antigens to such a low level that accurate assay therefor is quite difficult in an automated system whose entire purpose is to perform the assay reliably and in a relatively short time.

Although identical binders are used in the pre-incubation and in the chamber, it is possible to use different specific binders in such steps; e.g., an antibody in one and a naturally occurring binder in the other.

Typical antigens which are present in the serum in small amounts are triiodothyronine ($T_3$) and digoxin. By way of illustration, $T_3$ may be present in a range of 0.25 to 0.8 ng/ml of serum (hypo condition), 0.8 to 1.3 ng/ml of serum (normal condition), and 1.3–2.0 ng/ml of serum (hyper condition). Dilution of serum to reduce the concentration of plugging proteins also reduces the concentration of $T_3$. This renders it difficult to assay for the lower levels of $T_3$ if the serum initially has $T_3$ present only in the lower level. Thus the sensitivity for measuring low levels of $T_3$ is adversely affected by serum dilution.

By the present invention, the sensitivity of the assay for $T_3$ in serum is adequate to measure the hypo condition in a diluted serum sample.

This sensitivity in an automated assay from serum is achieved by a pre-incubation of the diluted sample with an antibody and a known amount of labeled antigen. The pre-incubation, in effect, pre-binds a portion of the antigen in the sample. The pre-incubation is conducted for a period of time sufficient to establish an equilibrium condition, usually 10 minutes to 3 hours or more. Pre-incubation may be conducted on an automated basis by known automated pipetting equipment. This aspect of the assay is in the nature of pretreating of the samples or standards to allow for the assay rapidly and reliably.

The separation, conducted automatically and quickly, involves flowing the mixture formed during pre-incubation through an immunoadsorbent which has the same kind of antibody bound to the support as was used in the pre-incubation, except that there is an excess of antibody. Effectively, the immunoadsorbent has an activity of 95% or more based on the amount of antigen in the serum, an excess which is substantially greater than the amount of free antigen present in the pre-incubated mixture. Thus, substantially all, e.g., 95% or more, of the free antigen passing through the immunoadsorbent is bound to the antibody bound to the substrate. It is to be understood that the pre-incubation step may be effected if desired with a binder different that the binder used in the chamber. For example, a serum protein; in particular, TBG, could be used in one and antibody in the other.

It has also been found that the binder in the chamber need not be at the maximum amount for all free ligand in the sample subsequent to the incubation, provided that the capacity of the binder is constant over the range of the standard curve. Thus, for example, 50% binding capacity could be adequate if the criteria of constant binding capacity over the range of the standard curve is met.

The free fraction passing through and the fraction freed by elution may be counted as described.

Thus, one aspect of the present invention is that binding on the immunoadsorbent is relatively rapid even though the pre-incubation or initial binding phase is comparatively slow. In a typical example for the assay of $T_3$, reagents were prepared as follows:

(a) The adsorption buffer used to introduce the sample was 0.05 M tris-HCl buffer, pH 9.2 containing 0.01% (W/V) bovine serum albumin.

(b) The eluting solution was 60% methanol in 0.01 M sodium phosphate buffer, pH 7.5.

(c) The rinse solution was 50% methanol in 0.01 M sodium phosphate buffer, pH 7.5

(d) The sample buffer was 0.05 M tris-HCl, 0.01% (W/V) bovine serum albumin, 160 microgram/ml of 8-anilino naphthalene-1 sulfonic acid (Na salt) (ANS), and 45 nC/ml $^{125}I$ labeled $T_3$ antigen, specific activity 3,000 mC/mg. Thus the sample buffer contains a known amount of labeled antigen.

Thyroid hormone free serum was prepared by stirring activated charcoal with the serum for 18 hours. The charcoal was removed by centrifugation followed by filtration of the serum through a 0.4 micron filter.

The charcoal removes the $T_3$ binding proteins which may compete with the $T_3$ antisera. Thus, the concentration of binding proteins may be restored by using more thyroid hormone free serum for the standards.

Standard solutions were prepared as follows:

Aqueous standard of known concentrations varying from 3.9 to 1000 picogram/ml were prepared in aliquots of sample buffer, (d), supra. To each 1.0 ml of aqueous standard there was added 50 microliters of thyroid hormone free serum to restore the concentration of binding proteins.

The antibody solution was prepared using $T_3$ specific antibody raised in rabbits against triiodothyroproprionic acid conjugated to bovine serum albumin. One microliter of antisera was diluted into 1 ml of adsorbtion buffer, (a), supra.

A filter is used to filter all samples and standards before introduction to the antibody chamber as described in U.S. Pat. No. 4,059,685, and whose disclosure is incorporated herein by reference. The lower support, or filter outlet consists of a nylon mesh (400) disc, Teflon wool disc and nylon mesh (400) disc. The body of the chamber was filled with glass wool.

The antibody chamber used in the assays is as described in Ser. No. 565,848 wherein the lower support, or exit end of the chamber, consists of nylon mesh (400) disc, a Teflon felt disc and a nylon mesh (400) disc. Antibody to $T_3$ conjugated to cyanogen bromide activated dextran coated Zipax was added to fill the chamber compartment. The upper support was a single Teflon felt disc.

Assays were conducted using the automated equipment as described in U.S. Pat. No. 4,009,005 and whose disclosure in incorporated herein by reference. The buffer pump speed was 1.00 ml/min.

In practice, assays involve generation of data from standard solutions using a specific antibody chamber, followed by assays of unknowns using the same chamber and reagents and process times used for the standards. The sequence involves adding to each 1.0 ml of standard solution (prepared above) in a polystyrene sample cup, 0.1 ml of diluted (1:1, 000) $T_3$ antisera, prepared as described. The total volume of the sample cup was 2 ml. The mixture was incubated, covered and in the dark for at least three hours at room temperature.

Unknowns were prepared for analysis by diluting 40 microliters of unknown serum with 1.0 ml of sample buffer in a serum cup, to which was added 0.1 ml of diluted $T_3$ antisera, prepared as described. The dilution of the unknown serum was 26 fold while the dilution of the $T_4$ free serum was 21 fold to adjust protein concentration. Following incubation of the unknown with the antibody, the free and bound antigen may be separated and counted using the automated equipment.

The labeled antigen is present in the sample buffer in a known amount. The reactions during an assay of a standard or unknown may be understood using the following symbols:

$Ag^*$ is labeled antigen; $Ag$ (S or W) is the standard or unknown unlabeled antigen; $Ab$ is the antibody; and $SS_{ab}$ is the immunoadsorbent. The sequence may be represented as follows:

In the sample cup (pre-incubation):

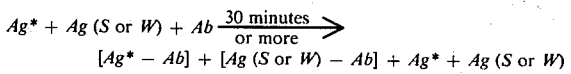

In the presence of the immobilized immunoadsorbent, the mixture resulting from pre-incubation forms two fractions, a free fraction (underlined) and a bound fraction, as follows:

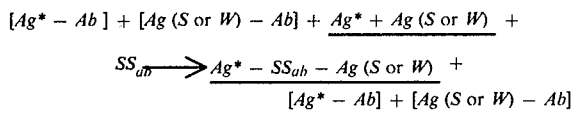

The bound fraction is pumped to the detector for counting and thereafter the free fraction is eluted from the antibody covalently bound to the solid support, as indicated in the following:

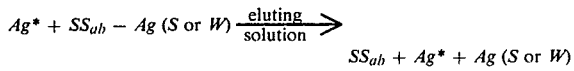

The released antigen is also pumped to the detector for counting.

Using the above described procedures, four clinical samples were run along with two sets of commercial serum control samples. Data from standards were also generated as shown in the following table.

$T_3$ DATA

| | Free | Bound | Total (7) | % Bound (8) | Assay pg/ml | Serum pg/ml |
|---|---|---|---|---|---|---|
| Blank (1) | 436 | 527 | | | | |
| Zero (2) | 4082 | 2805 | 5924 | 38.5 | | |
| Standard-3.9(3) | 3964 | 2908 | 5909 | 40.3 | | |
| Standard-7.8 | 3712 | 3084 | 5833 | 43.8 | | |
| Standard-15.6 | 3713 | 3297 | 6047 | 45.8 | | |
| Standard-31.2 | 3216 | 3646 | 5899 | 52.9 | | |
| Standard-62 | 2684 | 4302 | 6023 | 62.7 | | |
| Standard-125 | 2194 | 4573 | 5804 | 69.7 | | |
| Standard-250 | 1688 | 5183 | 5908 | 78.8 | | |
| Standard-500 | 1496 | 5417 | 5950 | 82.2 | | |
| Standard-1000 | 1306 | 5364 | 5707 | 84.8 | | |
| Blank (1) | 529 | 568 | | | | |
| Zero (2) | 4267 | 2781 | 6085 | 37.0 | | |
| Clinical (High) (4) | 3060 | 2851 | 5959 | 56.0 | 40 | 1040 |
| Clinical (Low) | 3491 | 3628 | 6156 | 50.4 | 24 | 624 |
| Clinical (High) | 2950 | 4186 | 6173 | 59.3 | 50 | 1300 |
| Clinical (Low) | 3567 | 3680 | 6284 | 50.2 | 24 | 624 |
| Commercial (Low) | 3995 | 3046 | 6078 | 41.4 | 5 | 130 |
| Commercial (Normal) | 3494 | 3570 | 6101 | 49.9 | 21 | 546 |
| Commercial (High) | 2605 | 4536 | 6178 | 64.9 | 76 | 1976 |
| Commercial (5) | 3385 | 3848 | 6270 | 53.0 | 32 | 832 |
| Commercial (6) | 2283 | 4701 | 6021 | 69.3 | 110 | 2860 |

(1) The blank contained no radioisotype but merely the components of the sample buffer less the labeled antigen. This blank provided background counts.
(2) This zero was the sample buffer without unlabeled $T_3$.
(3) Standard concentration expressed in picograms of $T_3$/ml.
(4) Clinical samples were of unknown concentration, but in the general ranges indicated.
(5) Commercial sample of a concentration of 700 pg $T_3$/ml ± 200
(6) Commercial sample of a concentration of 2,500 pg $T_3$/ml ± 400
(7) Calculated by subtracting the free and bound background counts from the free and bound net counts.
(8) Expressed in terms of percentage of antigen bound to the antibody covalently coupled to the solid support.

From the above data, it can be seen that there is good correlation between the determination made in accordance with the present invention, by automated equipment, and the actual concentration.

The above data also indicates the sequence used for generation of data from the standards, all of which are processed by the same procedure, and the same procedure used for the unknowns which include both the clinical and commercial samples.

In an assay for $B_{12}$, pre-incubation is effected employing 1 ml of sample buffer (Borate pH 9.3), 0.1 ml of sample or standard, 0.1 ml radiocobalt labeled $B_{12}$ and 0.1 ml intrinsic factor as binder. Incubation is effected for three hours at room temperature. The pre-incubated sample is then run through automated equipment as hereinabove described, except that the immobilized binder is toad fish serum covalently linked to cyanogen bromide activated dextran coated Zipax.

The bound $B_{12}$ (tracer and sample) passes through the chamber for counting, and free $B_{12}$ (tracer and sample) is retained on the binder in the chamber.

The bound portion is subsequently eluted with citrate phosphate buffer, pH 3.5, and counted.

In an assay for folic acid, pre-incubation is effected employing 1 ml of sample buffer (Borate pH 9.3), 0.1 ml of sample or standard 0.1 ml $^{125}$I-tyrosyl substituted folic acid as tracer and 0.1 ml milk binder. Incubation is effected for three hours at room temperature.

The pre-incubated sample is then run through automated equipment as hereinabove described, except that the immobilized binder is milk binder covalently linked to cyanogen bromide activated dextran coated Zipax.

The bound folate (tracer and sample) passes through the chamber for counting, and free folate (tracer and sample) is retained on the binder in the chamber.

The bound portion is subsequently eluted with citrate phosphate buffer, pH 4.0 and counted.

The advantage of the present invention is the ability to provide relatively rapid and accurate determinations directly from serum for antigens present in relatively small amounts by the use of automated equipment. The pre-incubation sequence not only reduces on machine time, but permits dilution of the serum so as to reduce substantially the concentration of plugging proteins present in serum. By use of pre-incubation, the sensitivity of the assay is increased substantially to the point where the ligand present in small amounts may be assayed accurately by a flow through system, as described.

It has been noted that ligands such as triiodothyronine and tetraiodothyronine tend to deposit on the surfaces of the various flow lines through which they flow, especially if the flow lines are of plastic material. The accumulation of $^{125}$I-$T_3$ or $^{125}$I-$T_4$ in the system may adversely affect the background counts. Thus, in accordance with this invention, a rinse solution is used to maintain low background.

A typical material usable as a rinse solution is 2% solution (by weight) of DMS in a 30% solution (by volume) of ethanol in water which cleans the radioactive counting flow cell only.

While the above invention has been described with reference to the examples as to specific ligands, it will be understood that the procedures herein described have applicability to those instances in which the ligand is present in relatively small amounts and with proteins which tend to create flow problems through a solid substrate binder.

It will also be apparent to those skilled in the art that various modifications and alternatives may be made without departing from the spirit and scope of the invention as set forth in the appended claims.

I claim:
1. In a process for automated radioassay of a ligand sample by flowing the sample through a chamber con- taining an immobilized binder composed of a solid substrate and binder specific to the ligand and wherein the sample contains proteins tending to plug the substrate, the improvement comprising:

diluting the sample to a consistency for free unplugged flow through the immobilized binder;

preincubating the sample with a binder specific to the ligand in said sample being assayed together with a known amount of a radioactive labeled ligand to form a mixture including (a) unlabeled ligand bound to the binder, (b) labeled ligand bound to the binder, (c) free unbound unlabeled ligand, and (d) free unbound labeled ligand;

providing a chamber containing a binder specific to the ligand supported on a solid substrate to bind free unbound labeled and unlabeled ligand;

flowing said mixture through said chamber to bind free unbound labeled and unlabeled ligand to the solid supported binder in the chamber with the bound labeled and unlabeled ligand passing through the chamber;

flowing an eluting solution through said chamber to effect release of labeled and unlabeled ligand from the solid supported binder in the chamber;

counting the radioactivity of at least one or both of the labeled ligand which passed through the chamber and the labeled ligand eluted from the chamber to determine the quantity of the ligand sought to be assayed in said sample; and rinsing the chamber for subsequent assays of other samples of the same ligand.

2. In a process as set forth in claim 1 wherein said sample is serum containing proteins tending to plug said chamber.

3. The process of claim 1 wherein the ligand is folic acid.

4. The process of claim 1 wherein the ligand is vitamin $B_{12}$.

5. In a process as set forth in claim 1 wherein said pre-incubation is conducted for a period of time sufficient to establish an equilibrium between the labeled and unlabeled ligand bound to the binder.

6. In a process as set forth in claim 1 wherein the solid substrate is a particulate substrate.

7. A process for the direct radioimmunoassay of $T_3$ antigen in a serum sample comprising the steps of preincubating a binder specific to $T_3$ antigen in the presence of radioactive labeled $T_3$ antigen and unlabeled $T_3$ antigen sample to form a mixture including (a) unlabeled $T_3$ bound to the binder, (b) labeled $T_3$ bound to the binder, (c) free unbound unlabeled $T_3$, and (d) free unbound labeled $T_3$;

passing said mixture through a chamber containing a binder specific to $T_3$ supported on a solid substrate to effect binding of the free unbound labeled and unlabeled $T_3$ to the supported binder while said bound labeled and unlabeled $T_3$ passes through said chamber;

flowing an eluting solution through said chamber to effect release of the labeled and unlabeled $T_3$ bound to the supported binder in the chamber;

counting the radioactivity of at least one of the labeled $T_3$ which passed through the chamber or labeled $T_3$ eluted from the chamber to determine the quantity of $T_3$ in said serum.

* * * * *